United States Patent

Rebuffat et al.

[11] Patent Number: 5,290,298
[45] Date of Patent: Mar. 1, 1994

[54] FRAGMENTABLE ANASTOMOTIC DEVICE

[75] Inventors: Carlo Rebuffat; Riccardo Rosati, both of Milan, Italy

[73] Assignee: United States Surgical Corporation, Norwalk, Conn.

[21] Appl. No.: 694,741

[22] Filed: May 2, 1991

[30] Foreign Application Priority Data

May 7, 1990 [IT] Italy .................. 20225 A/90

[51] Int. Cl.$^5$ .................. A61B 17/00
[52] U.S. Cl. .................. 606/153; 606/151
[58] Field of Search .............. 606/153, 151, 156, 155, 606/154

[56] References Cited

U.S. PATENT DOCUMENTS

| | | |
|---|---|---|
| 422,584 | 3/1890 | Finley .................. 52/586 |
| 3,519,187 | 7/1970 | Kapitanov et al. . |
| 4,128,264 | 12/1978 | Oldford .................. 285/238 |
| 4,552,387 | 11/1985 | Schmidt .................. 285/238 |
| 4,667,673 | 5/1987 | Li . |
| 4,931,057 | 6/1990 | Cummings et al. .................. 606/153 |
| 5,007,666 | 4/1991 | Kyfes .................. 285/373 |

FOREIGN PATENT DOCUMENTS 0362163  4/1990  European Pat. Off. ........... 606/154

Primary Examiner—Stephen C. Pellegrino
Assistant Examiner—J. Schmidt

[57] ABSTRACT

A fragmentable compression device for the anastomosis of hollow organs of the human body comprising free cylindrical members that are composed of sectors. The edges of the hollow organs to be anastomosed are compressed between the first and second members by means of the third member, which presses the second member against the first one. The first member is in turn composed of a first and second sub-members, said sub-members being composed of sectors the second one of said sub-members being locked within the first one by means of teeth that are present on the outer surface of the second sub-member, said teeth being inserted into notches that are carved out of the internal surface of the first sub-member.

9 Claims, 2 Drawing Sheets

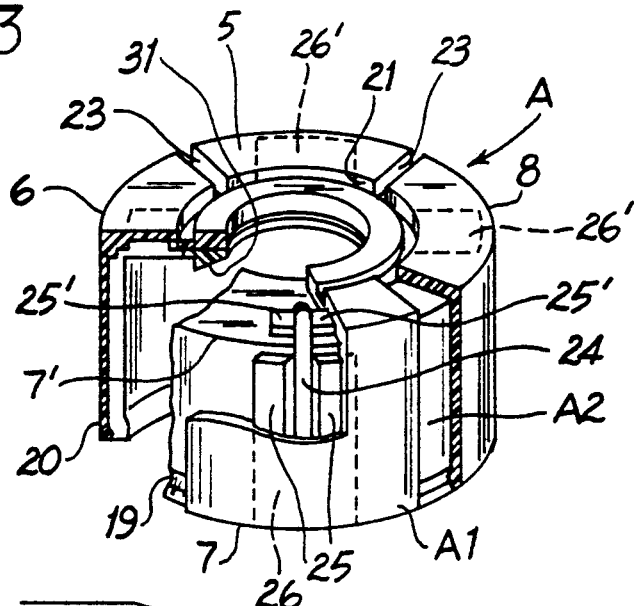
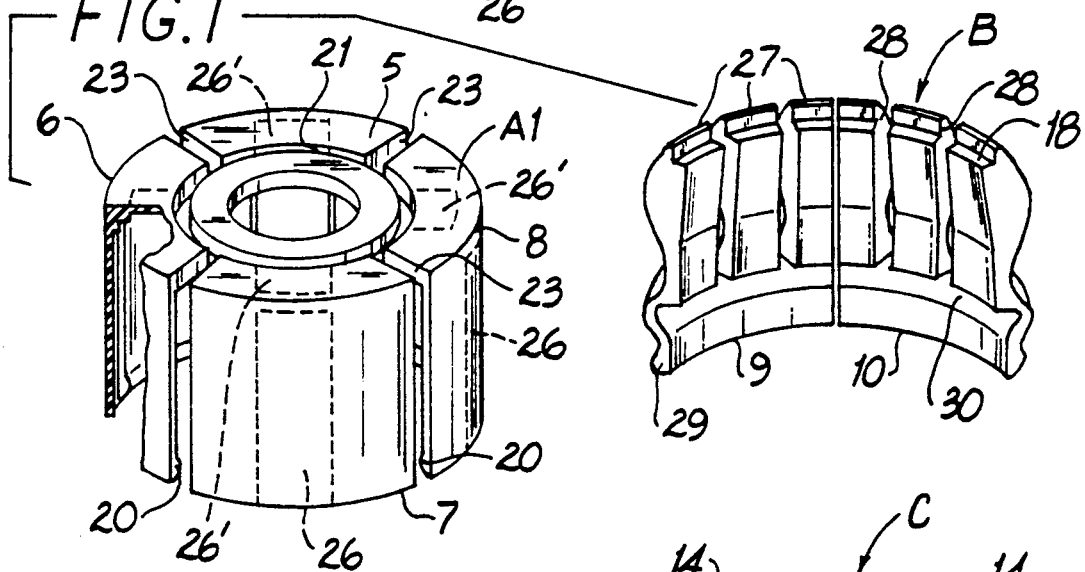
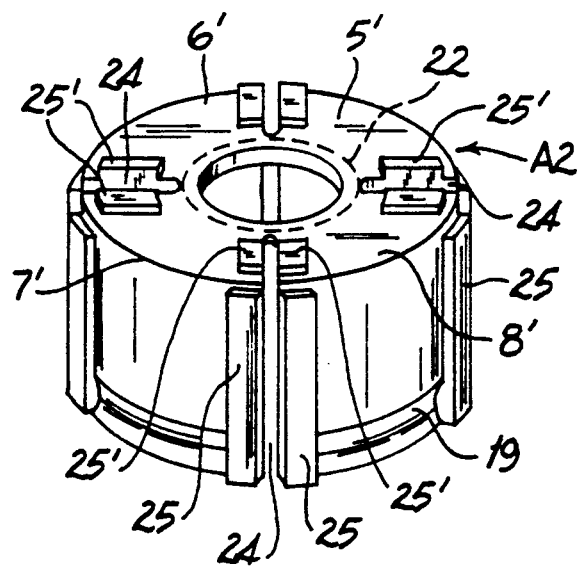
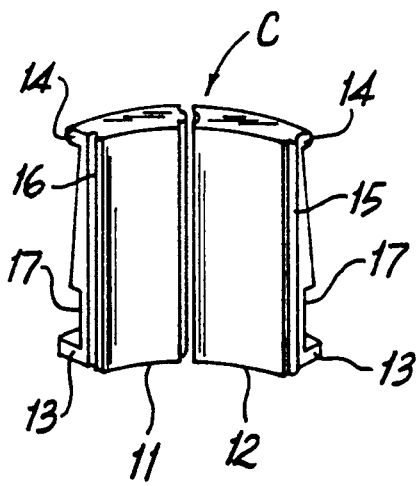

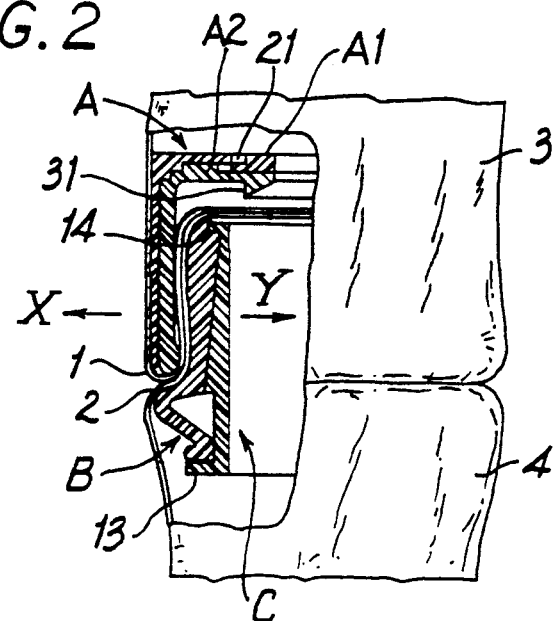
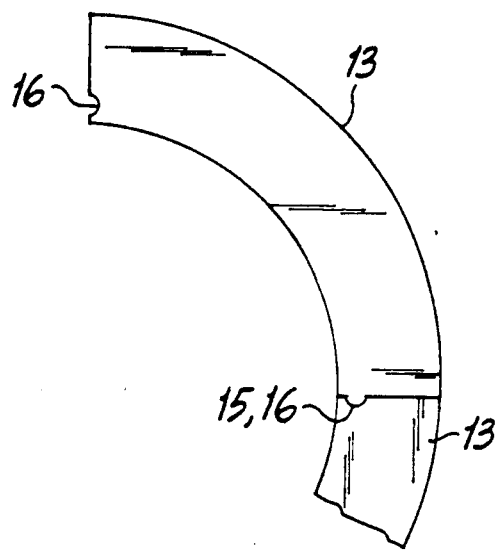
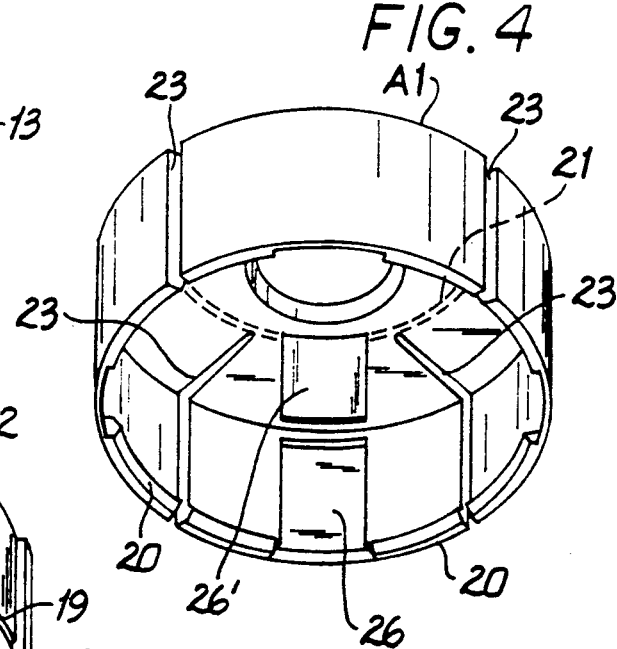
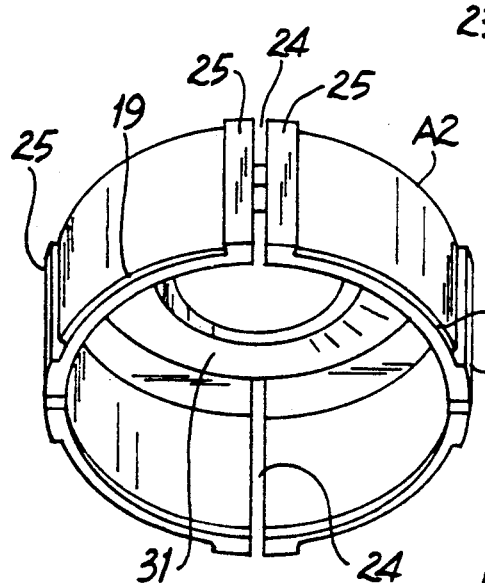

FRAGMENTABLE ANASTOMOTIC DEVICE

FIELD OF THE INVENTION

The present invention relates to a fragmentable compression device for the anastomosis of hollow organs of the human body, such as parts of the digestive tract, or intestine.

BACKGROUND OF INVENTION

Compression devices to carry out the anastomosis of said organs have been studied in the past. Said known devices are composed of biodegradable parts, that are suited to compress the edges of the hollow organs to be connected, so that said devices are reduced to fragments that can be more easily expelled with the stool. This technique is known for example from U.S. Pat. No. 3,974,835. The biodegradation rate of said materials varies from individual to individual and within the same individual according to the different physiological condition implying alteration of the metabolism and, therefore, a change in the rate of the chemical reactions causing the biodegradation. There is therefore a problem in that it can not be precisely forecast how much time will be necessary for the fragments of said devices to be reduced: in fact, it might even occur before, or a considerable time after, the natural consolidation of the edges of the organs to be anastomosed occurs. In both cases disadvantageous conditions would be created: in the first case the surgery would have failed because the holding device would be fragmented before the consolidation, that is no healing of the organs to be anastomosed would occur, and in the second case an obstacle would be introduced into the digestive tract in an unforeseeable seat and for a longer time than necessary.

Moreover, said devices made of biodegradable material must necessarily have thin walls, thereby having the draw-back of being very fragile and difficult to manufacture.

To the purpose of eliminating the above-mentioned draw-backs, a device has been studied and manufactured, said device being the object of the European patent application No 0362163 of the same inventors of the present application.

The above device, which exhibits the features of being reduced to fragments as soon as the edges of the organs to be anastomosed lose their consistency, is composed of a first member having a hollow cylindrical shape that is adapted to contain a second member, also having a hollow cylindrical shape, in such a way that between said two members the edges of said two hollow organs to be anastomosed can be inserted. In particular, the first member is composed of two sub-members that are lockingly inserted into one another. Such a device can easily be applied to an apparatus, such as the one described in U.S. Pat. No. 4,681,108, studied and manufactured by the same inventors of the present application, that allows the subject device to be positioned and, consequently, employed.

The above-mentioned sub-members are composed of sectors that are solidly connected to one another by means of teeth provided on the circumferential part of the sectors of the internal sub-member that are engaged in through-windows formed on the circumferential part of the sectors of the outer sub-member, thereby locking it onto the other sub-member.

Also this solution, while being a valid one in that it has improved the prior technology, exhibits some draw-backs, such as for example the instability of the anastomotic device. In fact, said device, while it warrants a good stability in the normal physiological and pathological state of the patient, if it is handled by the surgeon with insufficient caution, it can be fragmented, for example when the compressed tissue of the organs to be anastomosed is very this.

A further draw-back results from the need of using, for manufacturing its outer sub-member, a material having a high tensile strength since this sub-member comprises the above-mentioned windows that are the weak point of the device.

Moreover, it is very difficult and expensive to produce a mould for the mass production of said outer sub-member in plastic material.

SUMMARY OF THE INVENTION

An object of the present invention is to eliminate the above-mentioned draw-backs by providing a fragmentable compression anastomotic device for hollow organs having the following features:

it is mechanically stable, even under a rough handling by the surgeon, until the tissues compressed between the members of the device are necrotized;

it can be made of a plastic material not having an especially high tensile strength; it can be easily manufactured at a low price from plastic material by means of moulds.

Said objects are all achieved by the subject device, which comprises a first member, having a hollow cylindrical shape, which is adapted to receive a second member, having a hollow cylindrical shape, in such a way that between said two members the edges of two hollow organs to be anastomosed can be inserted, and a third member having a hollow cylindrical shape which is suited to press the second member against the first member, thereby compressing the edges of said hollow organs, each of the three members comprising sectors, said sectors being solidly connected to one another until said edges are present between the first and second members, and breaking-off to fragments when said edges are necrotized, the first member being composed of a first and second sub-members, the two sub-members being engagingly connected to one another, the second one within the first one, by means of locking means, and provided with radial slots, so that, with the use of a known apparatus for the positioning of said compression device, a circular blade of said apparatus dissects the two sub-members, thereby fragmenting them in sectors, with the characteristic feature that said locking means consist of teeth projecting from one of said sub-members into notches that are provided in the thickness of the other sub-member.

A further characteristic feature is that the first sub-member exhibits at least one notch on the internal surface of each sector and that the teeth are provided on opposite sides relative to each slot of the second sub-member and project from the outer surface of the sub-member, said sub-member being lockingly engaged within the first sub-member, said notches being provided in the thickness of said first sub-member.

Further characteristic features are that the first sub-member exhibits said notches on the internal circumferential surface of said sectors and the teeth project from the outer circumferential surface of the second sub-member, that the first sub-member exhibits said notches also on the internal upper surface of said sectors and the teeth project from the outer upper surface of the second sub-member, and moreover that said notches of the first sub-member extend to the lower edge of said sectors and the teeth similarly extend to the lower edge of the second sub-member.

BRIEF DESCRIPTION OF DRAWING

Further features and advantages of the invention will be evident from the following detailed description of a preferred, non exclusive embodiment of the subject device, said embodiment being shown in a merely illustrative, non limiting way in the enclosed figures, in which:

FIG. 1 is an exploded view showing the first and second sub-members forming the first member of the subject device, and the second and third member partly in section.

FIG. 2 is a vertical section view of the subject device applied to the hollow organs to be anastomosed.

FIG. 3 is a perspective view of the first member consisting of the two sub-members that are engagingly connected into one another.

FIG. 4 is a perspective view of the first sub-member from the inside thereof.

FIG. 5 is a perspective view of the second sub-member from the inside thereof and FIG. 6 is a plan view of a detail of the third member.

DETAILED DESCRIPTION OF EMBODIMENTS

Referring now to the figures, the subject device comprises a first member A having a hollow cylinder shape in which a second member B, also having a hollow cylinder shape, is received, and a third member C having a hollow cylinder shape that, when it is inserted into member B, applies a pressure against the same. Member A consist of the first sub-member A1 and the second sub-member A2 that can be engagingly inserted into one another, as can be seen from FIG. 3 that will be described hereinafter in detail.

Referring now to FIG. 2, the edges 1 and 2 of hollow organs 3 and 4 of the human body, such as parts of the digestive tract or the intestine, that are to be anastomosed, which are enclosed between the first and second members A and B, are compressed therebetween. Members A, B and C are inserted into the hollow organs 3 and 4 by means of suitable equipment, one of which, for example, is described in U.S. Pat. No. 4,681,108.

Each of members A, B and C is composed of sectors which are kept solidly connected to one another until the edges of the organs 3 and 4 present between the first and second members A and B, respectively, become necrotized, after which becomes separated and the device breaks off from the seat of anastomosis due to loss of consistency by the action of gastric juice. Therefore, this disintegration of the members A, B and C occurs after the anastomosis has been consolidated, whereby the fragmentation of the device is not affected by chemical reactions as it occurs, on the contrary, in the device of the prior art.

More precisely, as can be seen in FIGS. 1 and 3, sub-members A1 and A2 are composed of sectors 5, 6, 7, 8 and 5', 6', 7', 8', respectively.

Member B is also composed of sectors 90 and 10 brought closed to one another and, thus, similar sectors, not shown, complete the hollow cylindrical shape of member B.

Similarly, member C is composed of sectors 11 and 12 and similar sectors, not shown, complete the hollow cylindrical shape of member C. Each sector of member C is advantageously provided with lower projections 13 and upper projections 14 and, on a terminal edge, with longitudinal tongue 15 and, on the other terminal edge, with longitudinal groove 16, so that the projections 15 of each sector can be inserted into grooves 16 of the adjacent sectors, as can be seen from FIGS. 1 and 6. Sectors 11 and 12 are also provided with circumferential grooves 17.

The above-mentioned grooves 16 and tongues 15 are the releasable engagement means between adjacent sectors 11 and 12.

It is also noted that the sectors of each of members A, B and C can be in any number greater than 2.

As can be seen from FIG. 2, to carry out the subject anastomosis surgery, the two edges 1 and 2 of hollow organs 3 and 4 to be anastomosed are inserted between hollow members A and B that are pressed by hollow member C which is placed within member B with the circumferential tongue 14 of member C inserted within the circumferential groove 18 of member B. When edges 1 and 2 are interposed between members A and B, the sectors of which members A, B and C are composed are solidly connected to one another. This is due to the pressure applied by said edges onto member A, which is composed of sub-members A1 and A2 engagingly inserted into one another, in the direction of arrow X and onto members B and C as shown by arrow Y. Said arrows are directed in opposite directions and act onto said sectors in such a way as to keep members A, B and C as if they were rigidly made of one piece. As soon as the anastomosis is consolidated, just outside of the pressure area, created by the edges 1 and 2 such edges 1 and 2 nectrotize and lose their consistency, whereby and pressures are released and, consequently, the constraints between sector and sector are cleaved, whereby the sectors of the three members are separated and go to fragments that, freely moving within the intestine hollow, can be expelled with the utmost ease.

Sub-members A1 and A2 are engagingly inserted into one another with tongue 20 inserted in undercut 19, this locking means being present in the circumferential part of sub-members A1 and A2 respectively. Thus, member A is compact, easy to handle and to apply to an apparatus, such as is described for example in the above-mentioned U.S. Pat. No. 4,681,108, which allows the subject device to be positioned and, thereby, used.

At the moment of using said apparatus, a circular blade of the apparatus dissects sub-members A1 and A2 respectively along groove 21 and circumference 22: in this way, due to the radial slots 23 and 24 provided on said sub-members A1 and A2, these sub-members are automatically fragmented into the above-mentioned sectors, respectively.

Upon insertion of edges 1 and 2 of hollow organs 3 and 4 between members A and B, as shown in FIG. 2, said sectors 5, 6, 7, 8, and 5', 6', 7', 8', when there is a pressure between member A and member B, remain solidly connected to one another due to the teeth 25 present on the circumferential part of the adjacent sectors of sub-member A2 that are inserted into notches 26 provided on the circumferential part of the sectors of sub-member A1.

The teeth 25 are provided on opposite sides of the slots 24.

Also on the upper part of sectors 5', 6', 7', 8' of sub-member A2, teeth 25' are present, said teeth 25' being provided on the opposite sides of the slogs 24; and inside the upper part of sectors 5, 6, 7, 8 of sub-member A1, notches 26' are provided with which said teeth 25' engage.

In FIG. 3, there is clearly shown member A, which is composed of sub-members A1 and A2, said sub-members being engagingly connected by means of undercut 19 on member A2 that receives the tongue 20 on member A1 and by means of teeth 25, 25' that are inserted in notches 26 and 26', respectively.

Member B consists of sectors 9 and 10 which advantageously possess a high flexibility in that they are shaped according to tongues 27 from slots 28 extended downwards to base 29, the inner part of which exhibits the circumferential groove 30.

According to a characteristic feature of the present invention, notches 26 are provided in the thickness of the inner circumferential surface of sectors 5, 6, 7, 8, i.e. they are not through-notches, so which teeth 25, that are inserted in said notches 26, do not project from these notches.

Moreover, both teeth 25 and notches 26 extend to the lower edge of sub-members A2 and A1, respectively.

Analogously, teeth 25' provided on the upper surface of sectors 5', 6', 7', 8' of sub-member A2 are inserted into notches 26' provided in the thickness of the inner upper surface of sectors 5, 6, 7, 8 of sub-member A1.

Said characteristics of sub-members A1 and A2 provide the above-mentioned advantages of: stability, easy manufacture and low cost of the subject device.

Moreover, the inner upper surface of sub-member A2 is provided with a circumferential tongue 31 that acts as a counter-blade for the circular blade of the above-mentioned apparatus according to U.S. Pat. No. 4,681,180. Said circumferential tongue advantageously eases the cutting of exceeding edges of the hollow organs to be anastomosed.

Changes can be brought to the invention, especially practical and design changes, without departing from the scope of the invention as defined in the claims.

For example teeth 25, 25' might be provided inside sub-member A1 and notches 26, 26' might be provided on the outer surface of sub-member A2, the subject device still exhibiting the above-mentioned advantages.

We claim:

1. A fragmentable compression device for the anastomosis of hollow organs of the human body, comprising:
a first member and a second member, both having a hollow cylindrical shape, said first member receives the second member in such a way that between said two members the edges of two hollow organs to be anastomosed can be inserted, and a third member having a hollow cylindrical shape which is suited to press the second member against the first member, thereby compressing the edges of the hollow organs, each of the three members comprising sectors, said sectors being solidly connected to one another when the edges are present between the first and second members, and breaking-off to fragments when the edges are necrotized,
the first member being composed of first and second hollow cylindrical sub-members having both an upper surface and a lower edge,
locking means for engagingly connecting the two sub-members to one another with said second sub-member being within the first sub-member, said locking means consisting of teeth projecting from one of said sub-members into notches of the other sub-member, said notches being in the thickness of said other sub-member, said notches having a depth less than the thickness of said other sub-member; and
radial slots delimiting said sectors whereby, with the use of means for positioning said compression device, the means for positioning including a circular blade, the circular blade dissects the two sub-members, thereby fragmenting them in sectors.

2. A device ad claimed in claim 1, wherein each sector of the third member is provided, on a terminal longitudinal edge thereof, with a longitudinal tongue and, on another terminal longitudinal edge thereof, with a longitudinal groove, so that each longitudinal tongue of a sector couples with the longitudinal groove of the adjacent sector.

3. A device as claimed in claim 1, wherein the second sub-member has a circumferential tongue inside the upper surface acting as a counter-blade for the circular blade that carries out the dissection of the edges of the hollow organs and of the two sub-members.

4. A fragmentable compression device for the anastomosis of hollow organs of the human body, comprising:
a first member and a second member, both having a hollow cylindrical shape, said first member receives the second member in such a way that between said two members the edges of two hollow organs to be anastomosed can be inserted, and a third member having a hollow cylindrical shape which is suited to press the second member against the first member, thereby compressing the edges of the hollow organs, each of the three members comprising sectors, said sectors being solidly connected to one another until the edges are present between the first and second members, and breaking-off to fragments when the edges are necrotized,
the first member being composed of first and second hollow cylindrical sub-members having both an upper surface and a lower edge,
locking means for engagingly connecting the two sub-members to one another with said second sub-member being within the first sub-member, said locking means consisting of teeth projecting from one of said sub-members into notches of the other sub-member, said notches being in the thickness of said other sub-member,
radial slots delimiting said sectors whereby, with the use of means for positioning said compression device, the means for positioning including a circular blade, the circular blade dissects the two sub-members, thereby fragmenting them in sectors,
wherein the first sub-member has said notches on an internal circumferential surface of said sectors and the teeth project from an outer circumferential surface of the second sub-member, and the first sub-member also has said notches inside of said upper surface of said sectors and the teeth project from outside of said upper surface of the second sub-member.

5. A device as claimed in claim 4, wherein said notches of the first sub-member extend to a lower edge of said sectors and the teeth correspondingly extend to a lower edge of the second sub-member.

6. The device of claim 5, wherein said notches have a depth in the thickness of said other sub-member wherein the depth of said notches is less than the thickness of said other sub-member.

7. A device as claimed in claim 4, wherein the second sub-member has a circumferential tongue inside the upper surface acting as a counter-blade for the circular blade that carries out the dissection of the edges of the hollow organs and of the two sub-members.

8. A fragmentable compression device for the anastomosis of hollow organs of the human body, comprising:

a first member and a second member, both having a hollow shape, said first member receives the second member in such a way that between said two members the edges of two hollow organs to be anastomosed can be inserted, and means for pressing the second member against the first member, thereby compressing the edges of the hollow organs, each of the three members comprising sectors, said sectors being solidly connected to one another when the edges are present between the first and second members, and breaking-off to fragments when the edges are necrotized, the first member being composed of first and second hollow sub-members having both an upper surface and a lower edge, locking means for engagingly connecting the two sub-members to one another with said second sub-member being within the first sub-member, said locking means comprising teeth projecting from one of said sub-members into notches of the other sub-member, said notches being in the thickness of said other sub-member, said notches having a depth less than the thickness of said other sub-member; and radial slots delimiting said sectors whereby, with the use of means for positioning said compression device, the means for positioning including a circular blade, the circular blade dissects the two sub-members, thereby fragmenting them in sectors.

9. A device as claimed in claim 8, wherein the second sub-member has a circumferential tongue inside the upper surface acting as a counter-blade for the circular blade that carries out the dissection of the edges of the hollow organs and of the two sub-members.

* * * * *